United States Patent [19]

Nazarian et al.

[11] Patent Number: 5,368,554
[45] Date of Patent: Nov. 29, 1994

[54] BLOOD PUMPING SYSTEM WITH SELECTIVE BACKFLOW WARNING

[75] Inventors: Richard A. Nazarian, Golden Valley, Minn.; Marc H. Agnew, Encinitas; Daniel E. Schneider, Carlsbad, both of Calif.; Wilfred A. Mead, Williamston, Mich.

[73] Assignees: Minnesota Mining and Manufacturing Company, St. Paul, Minn.; ViaSat Incorporated, Carlsbad, Calif.

[21] Appl. No.: 979,181

[22] Filed: Nov. 20, 1992

[51] Int. Cl.$^5$ ............................................. A61M 37/00
[52] U.S. Cl. .................... 604/4; 128/DIG. 13; 604/5; 604/31; 364/413.01
[58] Field of Search ...................... 604/4–6, 604/31, 50, 65, 67, 118, 121; 623/3; 128/696, DIG. 13; 600/17; 340/572; 364/413.01, 413.02, 574, 803

[56] References Cited

U.S. PATENT DOCUMENTS

| | | | |
|---|---|---|---|
| 2,862,203 | 11/1958 | Skaraeus et al. | 343/18 |
| 2,986,731 | 5/1961 | Harmon | 343/17.1 |
| 3,011,053 | 11/1961 | Sev | 250/20 |
| 3,815,582 | 6/1974 | Schuette | 128/2.05 F |
| 3,882,861 | 5/1975 | Kettering et al. | 128/214 E |
| 3,887,919 | 6/1975 | Christensen et al. | 343/18 E |
| 3,982,535 | 9/1976 | Bahrton | 128/214 E |
| 3,992,709 | 11/1976 | Watanabe et al. | 343/7.5 |
| 4,060,485 | 11/1977 | Eaton | 210/87 |
| 4,063,551 | 12/1977 | Sweeney | 128/2.05 P |
| 4,080,966 | 3/1978 | McNally et al. | 128/214 E |
| 4,114,152 | 9/1978 | Wiedemann et al. | 343/7.7 |
| 4,148,314 | 4/1979 | Yin | 128/214 E |
| 4,231,366 | 11/1980 | Schael | 128/214 E |
| 4,309,993 | 1/1982 | Brown | 128/214 E |
| 4,373,525 | 2/1983 | Kobayashi | 128/214 E |
| 4,429,302 | 1/1984 | Van de Bult | 340/572 |
| 4,444,546 | 4/1984 | Pazemenas | 417/12 |
| 4,447,191 | 5/1984 | Bilstad et al. | 417/12 |
| 4,460,353 | 7/1984 | Deckert et al. | 604/31 |
| 4,498,901 | 2/1985 | Finch | 604/65 |
| 4,537,200 | 8/1985 | Widrow | 128/696 |
| 4,540,946 | 9/1985 | Sainz et al. | 328/167 |
| 4,542,657 | 9/1985 | Barber et al. | 73/861.25 |
| 4,589,822 | 5/1986 | Clausen et al. | 415/170 A |
| 4,596,254 | 6/1986 | Adrian et al. | 128/666 |
| 4,690,002 | 9/1987 | Hubbard et al. | 73/861.25 |
| 4,766,905 | 8/1988 | Namekawa | 128/663 |
| 4,770,185 | 9/1988 | Silverstein et al. | 128/661.08 |
| 4,778,445 | 10/1988 | Hubbard et al. | 604/4 |
| 4,781,525 | 11/1988 | Hubbard et al. | 415/30 |
| 4,863,425 | 9/1989 | Slate et al. | 604/65 |
| 4,899,760 | 2/1990 | Jaeb et al. | 128/696 |
| 4,989,609 | 2/1991 | Smith et al. | 128/661.08 |
| 4,993,418 | 2/1991 | Weaver et al. | 128/661.08 |
| 5,010,887 | 4/1991 | Thornander | 128/696 |
| 5,105,815 | 4/1992 | Hall et al. | 128/661.08 |
| 5,171,212 | 12/1992 | Buck et al. | 604/4 |

OTHER PUBLICATIONS

A submission dated Jul. 16, 1991 by Sarns 3M Healthcare to the Food and Drug Administration regarding a Delphin II Centrifugal System embodying the invention disclosed in the above-identified patent application.

*Primary Examiner*—Randall L. Green
*Assistant Examiner*—Rob Clarke
*Attorney, Agent, or Firm*—Marshall, O'Toole, Gerstein, Murray & Borun

[57] ABSTRACT

A blood pumping system and method in which a selective backflow warning is generated in response to the detection of a backflow condition only in the absence of electrical interference that could cause the generation of a false backflow warning. Detection of a backflow condition is performed by activating the transmitter and receiver of a flow detector to determine the direction of blood flow and detection of the electrical interference is performed by activating the receiver of the flow detector while the transmitter is not activated. If electrical interference that could cause the generation of a false backflow warning exceeds a threshold, the system does not generate a backflow warning.

22 Claims, 9 Drawing Sheets

BLOOD PUMPING SYSTEM WITH SELECTIVE BACKFLOW WARNING

BACKGROUND OF THE INVENTION

The present invention relates to a blood pumping system capable of generating a backflow warning to warn of blood backflow through a non-occlusive blood pump and selectively disabling the backflow warning when electrical interference would cause a false backflow warning to be generated.

Blood pumping systems are used in clinical situations, such as open-heart surgery, to provide blood circulation for the patient undergoing the surgery. A typical blood pumping system draws blood from a patient's venous system into a conduit connected to the inlet of a blood pump and pumps it back into the patient's arterial system via a conduit connected to the outlet of the blood pump. The conduit may be connected to other devices to provide blood filtering, heating, oxygenation, collection, etc.

While various types of blood pumps have been used in blood pumping systems, one particular type of pump that has been found to be generally advantageous is a centrifugal pump. Such a pump is described in U.S. Pat. No. 4,589,822 to Clausen, et al. One characteristic of centrifugal blood pumps is that they are "non-occlusive," which means that when connected to a conduit, the mechanical structure of the pump allows blood to flow in the direction opposite the blood pumping direction. As a result, even though a non-occlusive blood pump may be turned on and operating, blood may actually flow backwards through the pump in the wrong direction, which may have adverse consequences for the patient.

As is known, the primary adverse effect of such backflow is that air may be drawn into the blood within the pumping system and pumped into the patient when the blood flow is later reversed to the proper direction. If the perfusionist or doctor detects that air has been drawn into the pumping system, there are procedures to prevent the air from being pumped into the patient. However, these procedures are tedious and/or time-consuming. Moreover, the perfusionist or doctor may not notice that air has been drawn into the system.

Backflow occurs when the output pressure of the blood pump is exceeded by the load pressure of the patient. This load pressure depends on such factors as the resistance of the arterial and venous systems of the patient, which may vary with the physical size and age of the patient; the resistance of the external pumping system; the relative height of the patient with respect to the blood pumping system; etc. If for any reason the load pressure should happen to exceed the output pressure of the pump, backflow will occur.

Blood pumping systems have previously been designed to generate a backflow alarm to warn the perfusionist or doctor of blood backflow. An example of such a system is disclosed in U.S. Pat. No. 4,778,445 to Hubbard, et al.

Although it is desirable to generate a blood backflow alarm, false alarms may be generated due to electrical interference. One example of such interference is "Bovie" interference, which is caused by the use of an electrocauterizer unit during surgery. In such a unit, high-energy radio-frequency ("RF") radiation is used to heat the metal tip of the unit. The RF radiation can interfere with various electronic equipment typically used during surgery, including an electronic blood pumping system as described above.

Although the amount of electrical interference caused by an electrocauterizer unit can be reduced somewhat by using conventional electro-shielding techniques, that approach is generally inadequate. That is particularly true in the case of a blood pumping system utilizing a Doppler-type flowmeter, which is very sensitive to electrical interference due to the fact that such a flowmeter uses a transducer at the end of a relatively long cable, which tends to act as an antenna and the fact that the electrical signals the flowmeter utilizes to determine flow are typically of relatively small magnitude. Thus, when high energy electrical interference is encountered, it is difficult if not impossible to separate the small signals indicative of flow from the much larger signals caused by the electrical interference.

The generation of false alarms during surgery is problematic due to the unnecessary stress and annoyance induced in the operating room personnel and may also cause such personnel to lose confidence in the accuracy of the medical equipment that generates such an alarm.

SUMMARY OF THE INVENTION

The present invention is directed to a blood pumping system having a backflow warning system that selectively generates a warning of blood backflow only in the absence of electrical interference that could cause a false backflow alarm. The blood pumping system has a non-occlusive blood pump and a conduit that is connectable between the blood pump and a patient to enable venous blood flow from the patient to the blood pump and to enable arterial blood flow from the blood pump back to the patient. The blood pumping system also includes an electrical interference detector that detects the presence of electrical interference and a backflow warning generator that selectively generates a backflow warning upon the detection of a backflow condition only in the absence of electrical interference as determined by the electrical interference detector. As a result, false backflow warnings caused by electrical interference are reduced in number and/or eliminated altogether.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
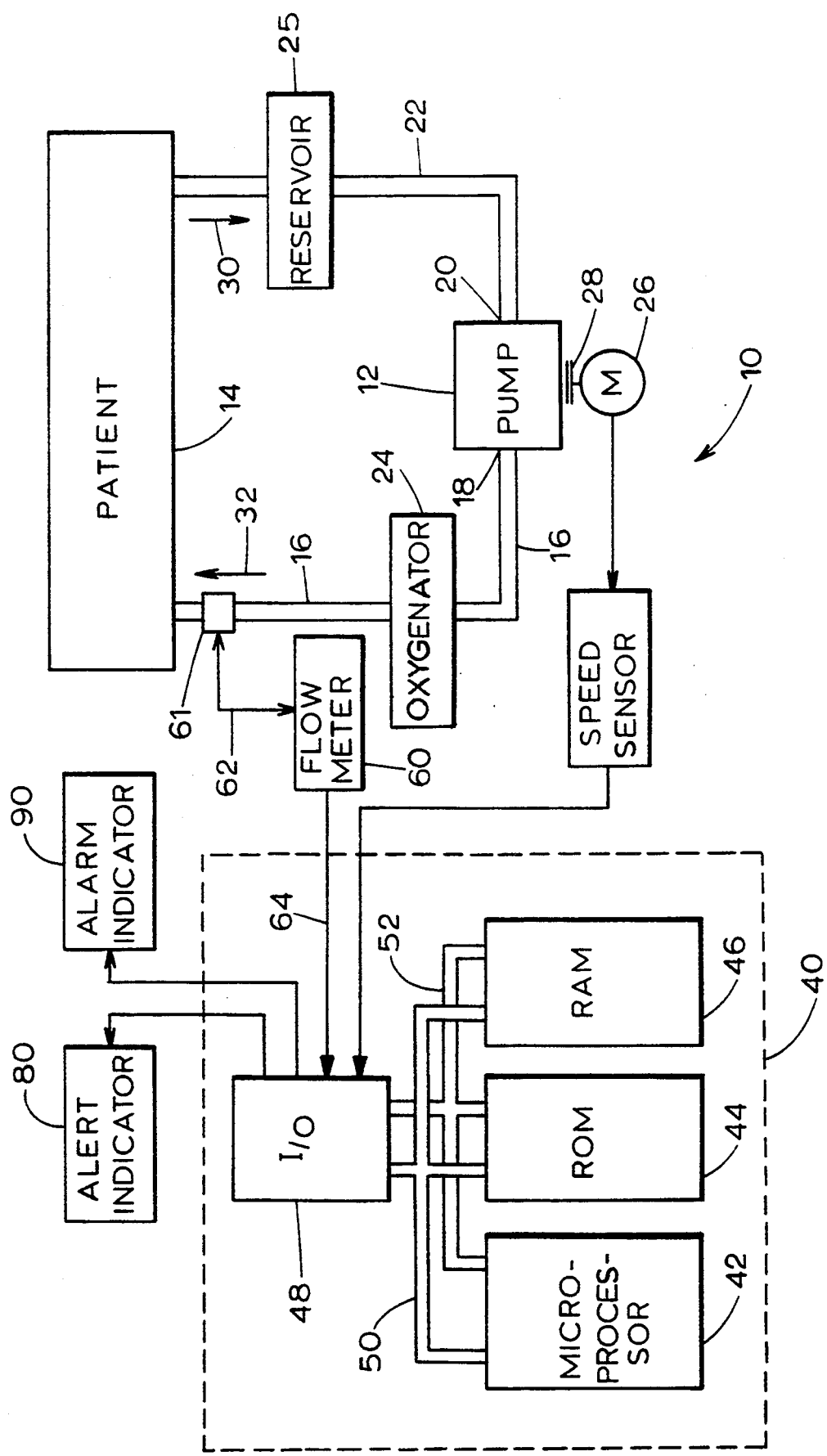
FIG. 1 is a schematic diagram of a blood pumping system in accordance with a preferred embodiment of the invention.

A preferred embodiment of a blood pumping system 10 is shown in FIG. 1. The blood pumping system 10 includes a non-occlusive blood pump 12 connected to the arterial system of a patient 14 via a conduit portion 16 connected to the outlet 18 of the pump 12. The inlet 20 of the pump 12 is connected to a conduit portion 22 that is connected to the venous system of the patient 14. A blood oxygenator 24 is connected to the conduit 16 to oxygenate the blood, and a reservoir 25 is connected to the conduit 22 to temporarily store excess blood.

The pump 12 is driven by a motor 26 coupled to the pump 12 via magnetic coupler 28. The pump 12 may be any type of non-occlusive pump, such as a centrifugal pump of the type disclosed in U.S. Pat. Nos. 4,589,822 or 4,984,972 to Clausen, et al., the disclosures of which are incorporated herein by reference.

In operation, blood is supplied from the patient 14 to the inlet 20 of the pump 12 via the conduit 22 in the direction of the arrow 30. The blood is pumped from the outlet 18 of the pump 12, through the oxygenator 24, and then to the arterial system of the patient via the conduit 16 in the direction of the arrow 32. The term "blood" as used herein is broadly defined to include blood, blood plasma, other blood constituents whether natural or artificial, and/or natural or synthetic fluids that may be used in blood pumping systems.

The blood pumping system 10 also includes a processing system 40 which may perform various functions relating to blood pumping systems, such as monitoring and/or controlling various conditions of the patient. The processing system 40 includes a microprocessor 42, a read-only memory (ROM) 44, a random-access memory (RAM) 46, and an input/output (I/O) circuit 48 which are interconnected by an address bus 50 and a data bus 52. The I/O circuit 48 may include conventional types of I/O circuits such as a bank of bidirectional buffers, a universal asynchronous receiver/transmitter (UART), etc.

The I/O circuit 48 is connected to receive a signal indicative of the blood flow through the conduit 16 from a flow measurement device 60, such as a flowmeter, via a line 64. The flowmeter 60 is connected via an electrical line 62 to a flow sensor 61. The electrical line 62 is relatively long, such as several feet, and may act as an antenna to attract undesirable electrical interference, which may include Bovie interference.

Two types of backflow warnings may be generated within the blood pumping system 10. A "backflow alarm" indicating that backflow is presently occurring can be indicated by an alarm indicator 90. A "backflow alert" indicating that backflow is imminent, but not yet occurring, can be indicated by an alert indicator 80.

The backflow alert and alarm may be any type of visual or audio indications such as flashing lights or buzzers. If both such warnings are used in the system, it is preferable that they be distinguishable from each other. A backflow alarm can be generated in any number of ways, including, for example, in accordance with U.S. Pat. No. 4,778,445 to Hubbard, et al., the disclosure of which is incorporated herein by reference, or where a directional flow sensor is used, simply by generating the alarm when the direction of blood flow is reversed.

A backflow alert can be generated in a number of ways, including, for example, in accordance with U.S. application Ser. No. 07/652,510 filed Feb. 8, 1991, now U.S. Pat. No. 5,171,212, the disclosure of which is incorporated herein by reference. The particular manner of generating either a backflow alarm or alert is not important to the practice of the present invention.

Figure 2:
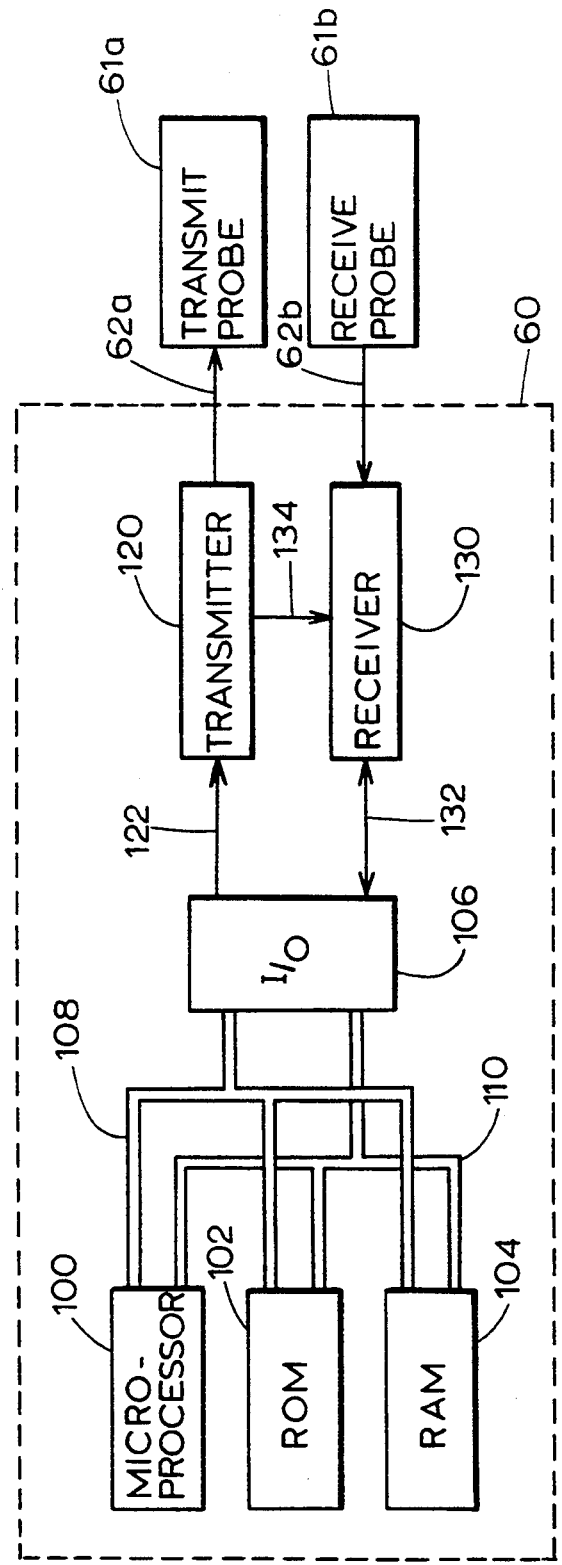
FIG. 2 is a block diagram of a flowmeter used in the blood pumping system in accordance with a preferred embodiment of the invention.

FIG. 2 is a block diagram of the flowmeter 60 shown schematically in FIG. 1. The flowmeter 60 includes a microprocessor 100, a ROM 102, a RAM 104, and an I/O circuit 106 which are interconnected by an address bus 108 and a data bus 110.

The flowmeter 60, which operates on the Doppler principle, includes a transmitter 120 coupled to the I/O circuit 106 via a transmit line 122. The transmitter 120 generates electrical excitation signals and transmits those signals to a transmit probe 61a via the line 62a. The transmit probe 61a converts those electrical signals into ultrasonic energy and radiates such energy into the conduit 16 through which blood is passing.

After being reflected by various constituents of the blood flowing through the conduit 16, the ultrasonic energy is detected by a receive probe 61b, which converts it into electrical signals and transmits those signals to a receiver 130 via a line 62b. The receiver 130 is coupled to the I/O circuit 106 via a line 132 and to the transmitter 120 via a line 134.

As is well known, the difference in frequency between the transmitted energy and the received energy is indicative of the magnitude of blood flow in accordance with the Doppler principle.

One particular manner of attaching the transmit and receive probes 61 to the conduit 16 is illustrated in U.S. Pat. No. 4,989,609 to Smith, et al., the disclosure of which is incorporated herein by reference.

Transmitter

Figure 3:
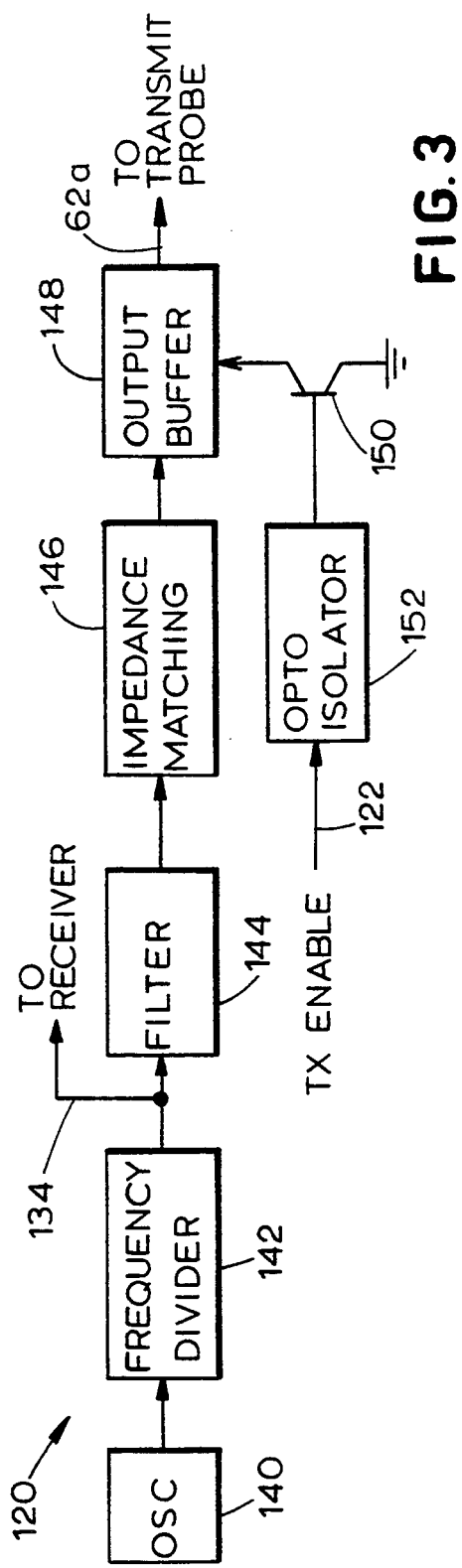
FIG. 3 is a block diagram of a transmitter used in the flowmeter of FIG. 2.

A block diagram of the transmitter 120 is shown in FIG. 3. The transmitter 120 selectively generates a high-frequency excitation signal, such as 4 MHz, which is transmitted to the transmit probe 61a. The excitation signal is generated by an oscillator 140 and a frequency divider 142. The excitation signal is filtered by a filter 144, transmitted to an impedance matching circuit 146, and then transmitted to an output buffer 148. The excitation signal is selectively transmitted to the transmit probe 61a via the line 62a under the control of a transistor switch 150 that is controlled by a transmit-enable signal on the line 122. An optical isolator 152 provides electrical isolation between the transmitter 120 and the I/O circuit 106. Although one manner of generating the transmitter excitation signal is described, the particular manner of generating that signal is not considered to be important to the invention.

Receiver

Figure 4:
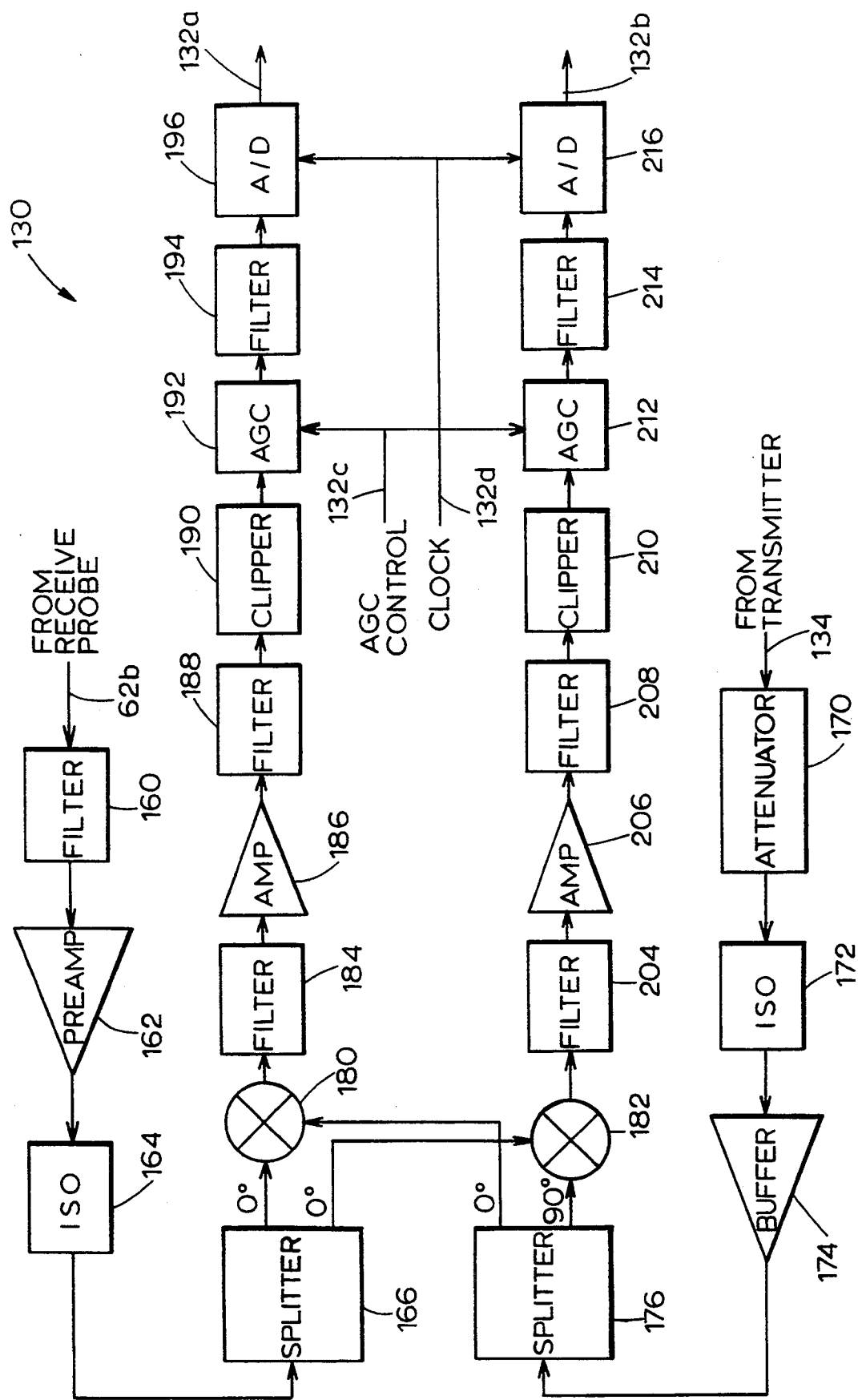
FIG. 4 is a block diagram of a receiver used in the flowmeter of FIG. 2.

A block diagram of the receiver 130 is shown in FIG. 4. The basic function of the receiver 130 is to generate a set of real and imaginary digital time domain samples in response to the output of the receive probe 61b and the transmitter excitation signal. As described below, the time domain samples are used by a conventional fast Fourier transform ("FFT") routine which generate a set of frequency domain samples therefrom. The particular manner of generating the time domain samples as shown in FIG. 4 is not considered to be important to the invention.

Referring to FIG. 4, the receive signal generated by the receive probe 61b is filtered via a filter 160 and amplified by a pre-amplifier 162. The receive signal is provided to a splitter circuit 166, which is electrically isolated from the pre-amplifier 162 via an isolation circuit 164. The transmit signal generated by the transmitter 120 is also provided to the receiver 130 via the line 134. The transmit signal is attenuated by an attenuator circuit 170, isolated via an isolation circuit 172, and provided to a splitter circuit 176 via a buffer 174.

The splitter circuit 166 splits the receive signal into two signals nearly identical thereto, except that the magnitude of the split signals is about one-half that of the original signal. The split receive signals generated by the splitter 166 also have the same phase as each other and as the original receive signal. The splitter circuit 176 performs the same function on the transmit signal, except that the phase of one of the split transmit signals is delayed by 90° with respect to the phase of the other split transmit signal.

One of the split receive signals and the undelayed split transmit signal are provided to a mixer 180, a conventional circuit for combining signals, which generates the "real component" of the signal. The other split receive signal and the delayed split transmit signal are provided to a mixer 182, which generates the "imaginary component" of the signal.

The signal output from the mixer 180 is transmitted to a filter 184 to remove the high frequency excitation signal, leaving a Doppler signal whose frequency is related to the flow magnitude. The Doppler signal is provided to an amplifier 186 and to a second filter 188 for further amplification and filtering. A clipper circuit 190 limits the magnitude of the Doppler signal to predetermined limits to prevent large signal transients, such as those caused by air bubbles, from damaging the circuitry. After clipping, the Doppler signal is provided to an automatic gain-control circuit 192 for selectively amplifying the Doppler signal and then to another filter 194. The Doppler signal is then sampled at a relatively high rate, such as 40 kHz, by an analog-to-digital (A/D) converter 196 to generate a large number of real time domain samples on the line 132a.

The signal output from the mixer 182 is processed in a manner similar to the signal output by the mixer 180 by components 204–214. The Doppler signal output from the filter 214 is sampled by an A/D converter 216, at the same rate as the A/D converter 196, to generate a large number of imaginary time domain samples on the line 132b.

Although conventional shielding techniques are generally insufficient to prevent Bovie interference, such techniques may nevertheless be utilized. Such techniques include splitting the circuitry into different sections, isolating the different sections via isolation transformers and radio-frequency interference (RFI) shields, powering the different sections by different power supplies, providing separate ground planes for the different sections, and/or using voltage regulators, inductor beads and low pass filters on the power supply lines.

General Operation

Figure 5A:
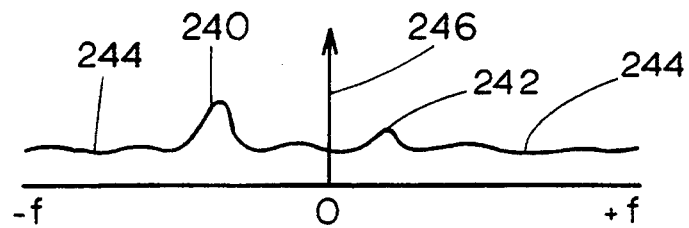
FIGS. 5a–5c illustrate several examples of electrical interference and how such interference may affect a Doppler signal that corresponds to fluid flow.
Figure 5B:
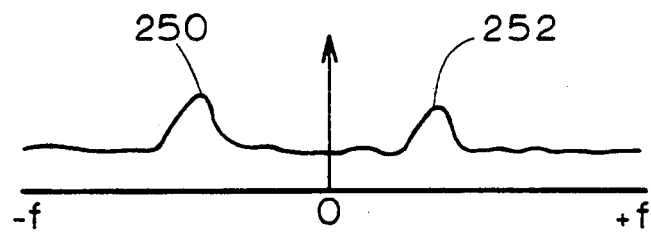
Figure 5C:
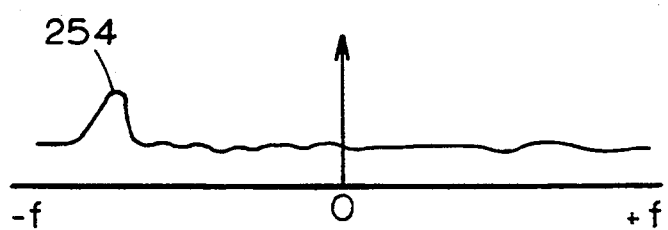

The signals generated by the receiver 130 that represent the flow magnitude can be adversely affected by the presence of electrical interference. FIGS. 5a–5c illustrate several examples of such electrical interference and how such interference may affect a Doppler signal that corresponds to fluid flow.

FIG. 5a illustrates a Bovie interference signal 240, a Doppler signal 242 that represents fluid flow, and background or white noise 244. The Doppler signal 242 is shown to have a positive frequency, meaning that it corresponds to positive fluid flow. The Bovie signal 240 is shown to have a negative frequency, meaning it would correspond to negative flow if it were erroneously interpreted to be a Doppler signal. The zero frequency at which there would be zero flow is represented by an arrow 246. In the example represented by FIG. 5a, absent some manner of detecting Bovie signals, the Bovie signal 240 could be erroneously interpreted to be the Doppler signal, instead of the real Doppler signal 242, thus causing a false backflow alarm to be generated.

Two other examples of how Bovie signals could occur are shown in FIGS. 5b and 5c. In FIG. 5b, a first Bovie signal 250 is shown to have a negative frequency, and a second Bovie signal 252 is shown to have a positive frequency (no Doppler signal is shown). In FIG. 5c, two Bovie signals 254, 256 are shown to both have negative frequencies. The Bovie signals shown in FIGS. 5b and 5c could also result in false backflow alarms. FIGS. 5a–5c are merely exemplary of how Bovie signals might occur and do not purport to cover all situations.

In general, Bovie signals are detected by the flowmeter by periodically reading the receiver 130 without activating the transmitter 120. In that case, since the transmitter 120 is not activated, the only signal appearing at the receiver 130 should represent white noise (designated 244 in FIG. 5a) and Bovie interference, if such interference is present.

The specific manner in which Bovie interference is detected and accounted for is described below in connection with FIGS. 6–10, which are flowcharts of a computer program that may be stored in the ROM 102 and executed by the microprocessor 100. Portions of the computer program could be stored in the ROM 44 and executed by microprocessor 42.

Main Routine

Figure 6:
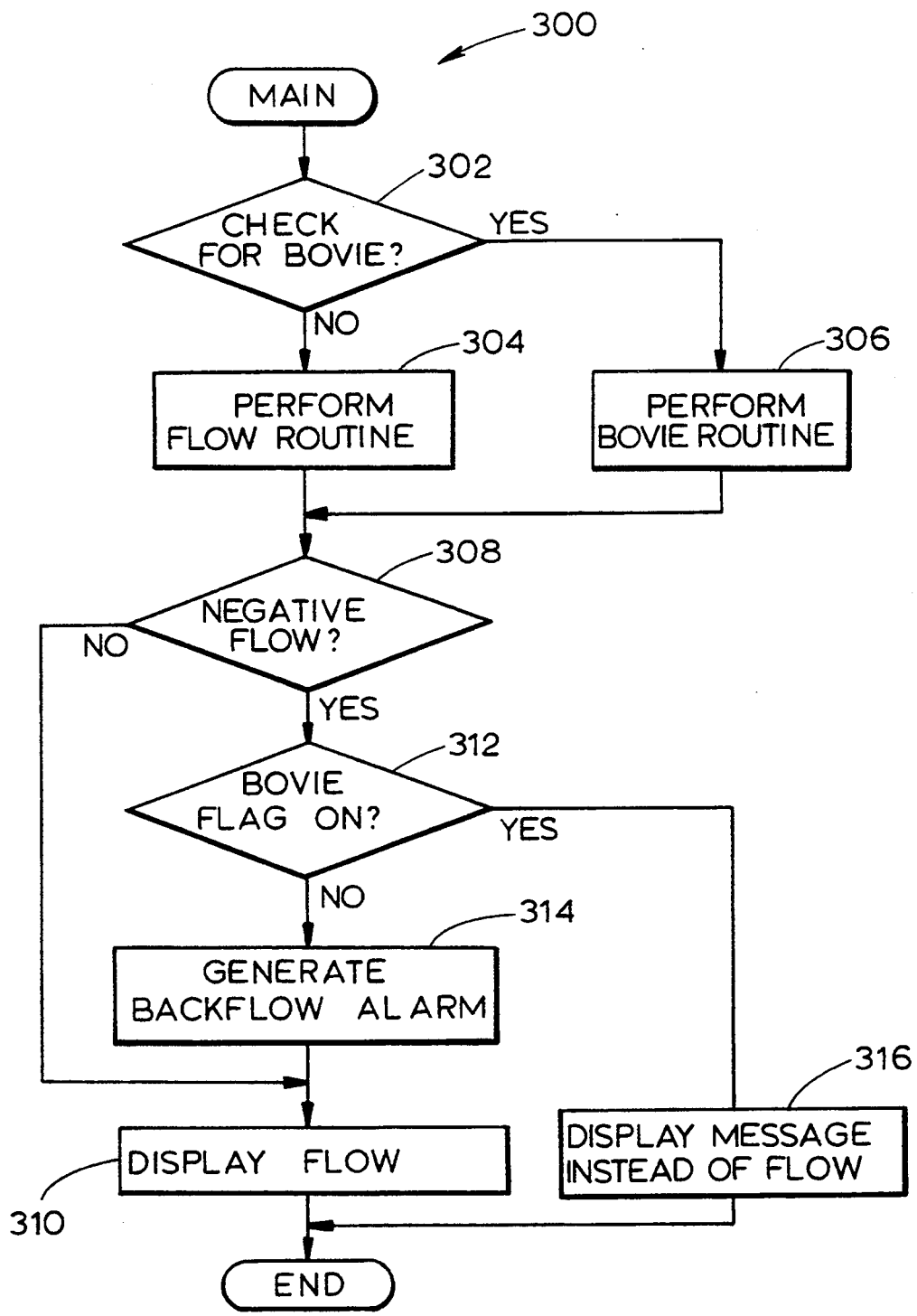
FIG. 6 is a flowchart of the overall operation of the flowmeter of FIG. 2.

Referring to FIG. 6, a main operating routine 300 is shown. During steps 302–306, the main routine either performs a flow routine, during which the transmitter 120 and receiver 130 are simultaneously activated to determine the flow magnitude, or a Bovie routine, during which only the receiver 130 is activated while the transmitter 120 is silent in order to detect any electrical interference.

There are a number of ways in which the performance of the flow and Bovie routines can be scheduled. A fixed schedule may be utilized, whereby the flow routine is performed a fixed number of times, e.g. five times, each time the Bovie routine is performed. Alternatively, a flexible schedule may be used whereby the Bovie routine is performed under certain circumstances. In any case, the Bovie routine should be periodically performed to detect the presence of electrical interference.

After the flow routine is performed at step 304 or the Bovie routine is performed at step 306, the routine branches to step 308. At step 308, if the flow magnitude (the average flow as determined during the flow routine as described below) is not negative, meaning that no backflow alarm will be generated, regardless of whether or not Bovie interference is present, the routine branches to step 310, where the fluid flow (the average fluid flow determined during the flow routine as described below) is displayed on the flowmeter display (not shown).

At step 308, if the flow is negative, the routine branches to step 312. At step 312, if Bovie interference is not present, as indicated by a Bovie flag not being on, the routine branches to step 314 where a backflow alarm is generated since the flow was negative and there was no Bovie interference detected.

At step 312, if Bovie interference was detected, the routine branches to step 316, thus bypassing the backflow alarm generation step 314, and causes a message to be displayed instead of the flow magnitude, since the flow magnitude is likely to be erroneous due to the presence of the detected electrical interference. The displayed message could be, for example, a textual message that Bovie interference was detected or simply a numeric display having a value outside the normal operating range of the flowmeter. As can be appreciated from the foregoing description, steps 308, 312 and 314 act as a backflow warning generator that selectively generates a backflow warning upon the detection of a backflow condition only in the absence of electrical interference that could cause a false backflow warning.

Flow Routine

Figure 7:
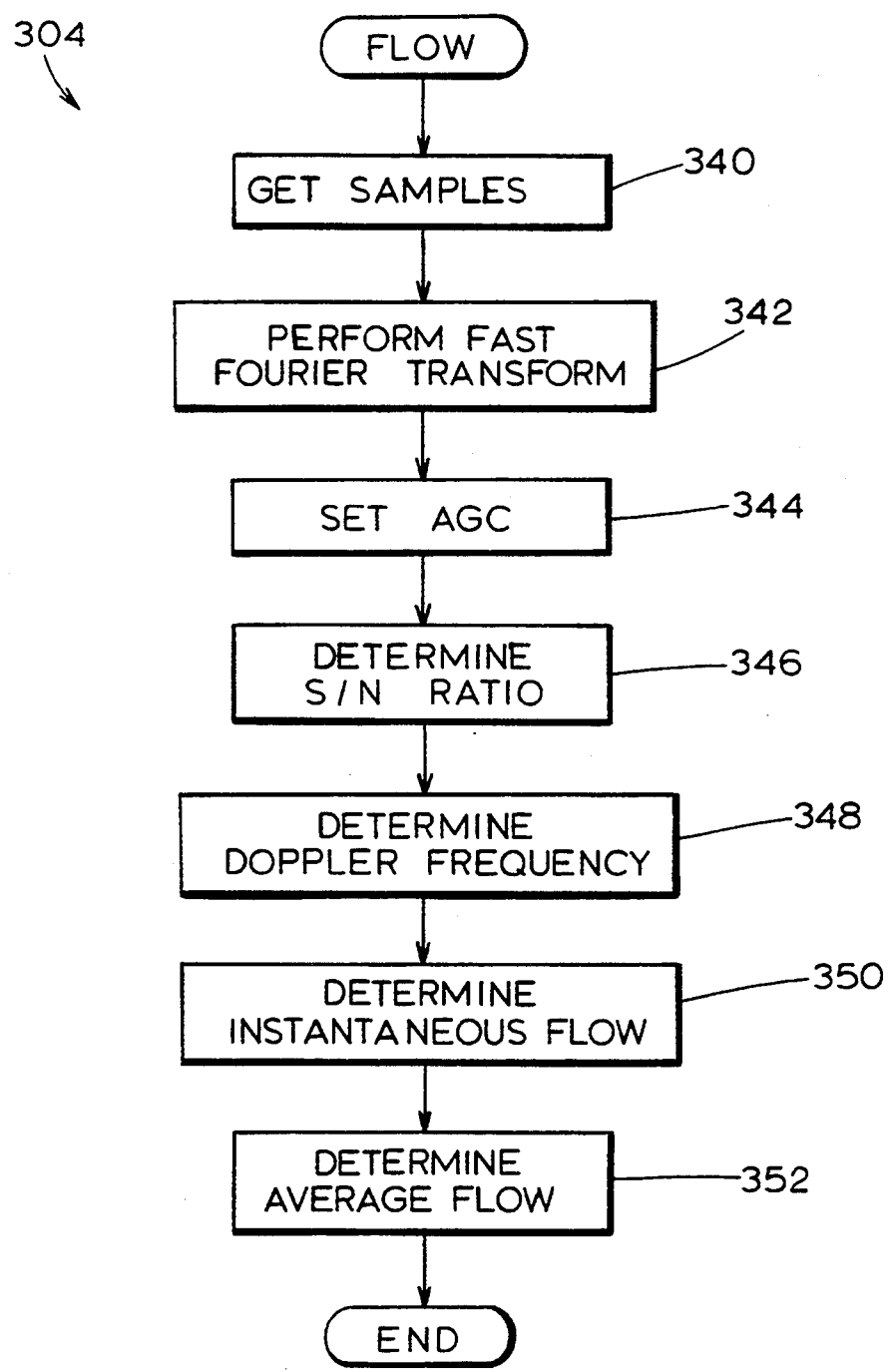
FIG. 7 is a flowchart of flow routine shown schematically in FIG. 6.

FIG. 7 illustrates a flowchart of the flow routine schematically shown as step 304 in FIG. 6. The first step of the flow routine retrieves a predetermined number, such as 1,024, of the real and imaginary Doppler samples from the A/D converters 196, 216. These samples are referred to herein as "time domain" samples since they are samples periodically taken over a period of time.

At step 342, a fast Fourier transform ("FFT") is performed on the time domain samples to generate a set of frequency domain samples. The FFT is accomplished in a conventional manner based on an FFT routine disclosed in Texas Instrument's Digital Signal Processing Applications with the TMS320 Family, which is incorporated herein by reference. Such a routine is also referred to in U.S. Pat. No. 4,989,609 to Smith, et al., the disclosure of which is incorporated by reference herein. The FFT routine is coded in assembly language for increased speed of operation. The result of the FFT routine is a set of 1,024 samples referred to as "frequency domain" samples. Each sample has a magnitude represented by a binary number for a particular frequency ranging from −20 kHz to 20 kHz, with each sample being spaced approximately 39 Hz apart, for the case of a 40 kHz sample clock on line 132d. The frequency represents the Doppler frequency. Thus, samples located at negative Doppler frequencies would correspond to negative flow rates, whereas samples located at positive Doppler frequencies would correspond to positive flow rates. Not all of the frequency samples generated at step 342 need to be used. For example, some of the samples may be ignored by using only the samples generated between ±10 kHz, or about half the samples generated.

Figure 8:
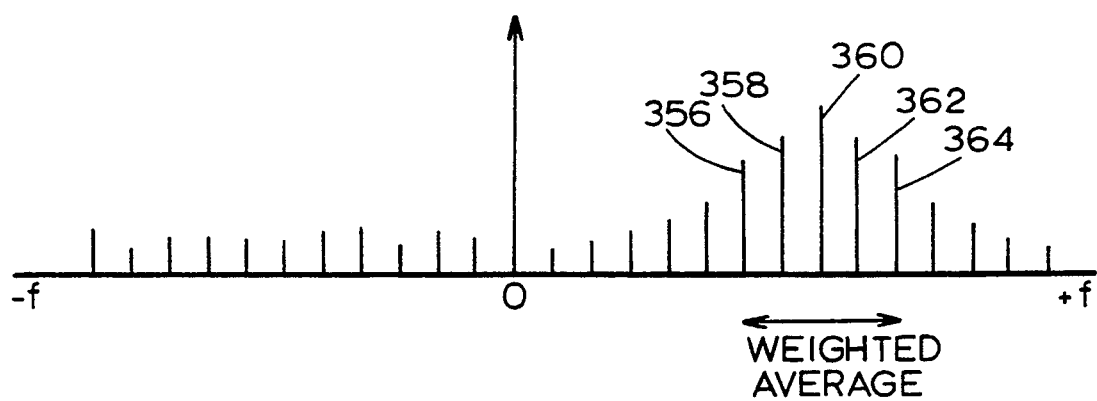
FIG. 8 is an illustration of a number of frequency samples generated as a result of a fast Fourier transform.

A number of frequency domain samples are illustrated in FIG. 8. As illustrated, the samples vary in magnitude, generally increasing towards a peak at the sample designated 360 at a positive frequency. Thus, the samples of FIG. 8 would result in a positive flow determination as described in more detail below.

Referring back to FIG. 7, at step 344, the level of automatic gain control is determined for the next execution of the flow routine 304. The AGC level is controlled via the line 132c connected to the AGC circuits 192, 212. One method of automatic gain control that could be used would utilize an AGC circuit that provides a number of discrete amplification levels, such as 0.5 dB steps. The discrete amplification level could be chosen so as to hold relatively constant the average signal energy of each of the time domain samples generated by the A/D converters 196, 216. Any other method of automatic gain control could also be used.

At step 346, the signal-to-noise ("S/N") ratio of the overall Doppler signal as represented by the frequency domain samples is determined. The S/N ratio is determined as follows. First, the magnitudes of all the frequency samples having a negative Doppler frequency are added together to generate a negative frequency power sum. Similarly, the magnitudes of all the frequency samples having a positive Doppler frequency are added together to generate a positive frequency power sum. Next, the smaller of the two power sums is subtracted from the larger to generate a power difference. That power difference is then divided by twice the magnitude of the smaller of the two power sums, and the logarithm of the resulting quotient is taken to determine the S/N ratio in decibels. The following equation summarizes the foregoing method:

$$S/N \text{ Ratio} = 10 \log [(Power_1 - Power_2)/(2 * Power_2)],$$

where $Power_1$ represents the total power of the side of the frequency spectrum having the larger power and $Power_2$ is the side of the frequency spectrum having the smaller power.

As can be seen from FIG. 8 and the foregoing description, in cases where there is a well-defined power peak, the S/N ratio will be relatively large. Where there is no discernable power peak, the S/N ratio will be relatively small.

At step 348, the Doppler frequency is determined from the frequency domain samples generated during step 342. The Doppler frequency generally corresponds to the frequency at which the frequency samples have the largest magnitude. As shown in FIG. 8, the Doppler frequency is generally represented by the frequency of the sample designated 360.

The Doppler frequency could be determined in numerous ways. The peak of the frequency domain samples could be determined by locating the sample having the largest magnitude. Alternatively, to eliminate spurious peaks, the peak could be determined by locating the three adjacent samples having the largest total magnitude, referred to as the three-sample peak. In the case of FIG. 8, both the single-sample peak and three-sample peak would be the frequency represented by the sample designated 360.

After the peak is determined, frequency averaging could be performed to further refine the frequency determination. For example, an average, weighted by sample magnitude, of all samples within a predetermined sample range of the peak could be generated. The predetermined range could include all samples having a relative minimum amplitude with respect to the magnitude of the peak sample. Thus, as shown in FIG. 8, the average Doppler frequency might be determined by computing a weighted average of the five samples designated 356–364.

In addition to the foregoing, a high pass filter might be used to cancel low frequency hump noise generally in accordance with the teachings of U.S. Pat. No. 4,993,418 to Weaver, et al., the disclosure of which is incorporated herein by reference. Many other ways of determining the Doppler frequency could be used.

After the Doppler frequency is determined at step 348, the instantaneous flow represented by that Doppler frequency is determined at step 350, if the S/N ratio of the signal as determined at step 346 surpasses a threshold level. If the S/N ratio does not surpass the threshold, thus indicating a Doppler signal with no relatively well-defined peak, the instantaneous flow is set to zero. Otherwise, the instantaneous flow is determined based upon the frequency-to-flow characteristics of the transmit and receive probes 61 that are used. For example, a probe might have a constant frequency-to-flow characteristic of 40 Hz/LPM. Other probes might have non-constant, but linear frequency-to-flow characteristics.

At step 352, the average flow over a period of time is determined based upon a number of instantaneous flow values. One purpose of generating an average flow is to generate a visual display of the flow that changes relatively smoothly without quickly jumping around between different flow values. The average could be determined by simply averaging a predetermined number, such as 20, of successive instantaneous flow values. Alternatively, a predetermined number of instantaneous flow values could be initially averaged, and then the average could be refined by only averaging the flow values within a predetermined limit of the initial average, such as the flow values within two standard deviations of the initial average. This latter approach would tend to filter spurious instantaneous flow values from a tight grouping of flow values (representing steady flow) while including all instantaneous flow values in a loose grouping (representing changing flow).

Other minor refinements could be utilized. For example, if more than half of the instantaneous flow samples are zero, than the average flow could be set to zero. In addition, the average flow could be rounded to the nearest 0.05 liter-per-minute (LPM) if the average flow is less than 1.5 LPM or to the nearest 0.1 LPM if the average flow is greater than 1.5 LPM.

Bovie Routine

Figure 9:
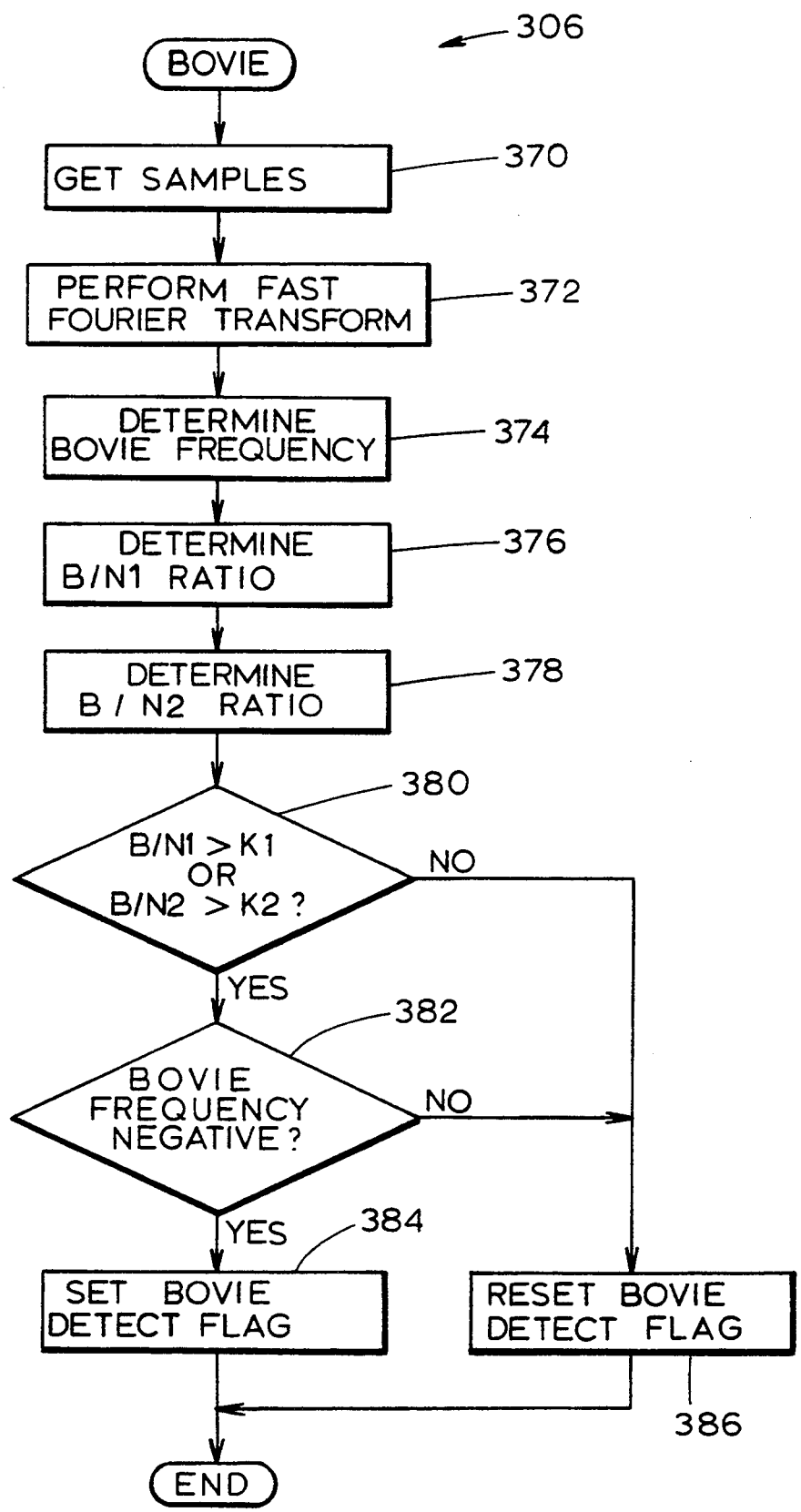
FIG. 9 is a flowchart of Bovie routine shown schematically in FIG. 6.

FIG. 9 illustrates a flowchart of the Bovie routine schematically shown as step 306 in FIG. 6. The Bovie routine 306, along with the receiver 130, act as an electrical interference detector to detect electrical intereference that could cause a false backflow warning.

Referring to FIG. 9, the get samples step 370 and perform fast Fourier transform step 372 are the same as corresponding steps 340–342 of the flow routine 304, except that the transmitter 120 is not activated while the time domain samples used in the Bovie routine are generated by the A/D converters 196, 216. Since the transmit probe 61a may continue to generate energy due to ringing for a short period of time after the transmitter 120 is turned off, the get samples step 370 should not be performed until that short ringing period has elapsed.

At step 374, the Bovie frequency is determined in a manner analogous to that described above in connection with step 348 of the flow routine. If a three-sample peak is used, the length of time required to determine such peak may be shortened by searching only that side of the frequency spectrum that has the most energy, as determined by the sum of the frequency domain samples on each side of the frequency spectrum.

Steps 376–380 act as a threshold detector that searches for and detects the presence of electrical interference. Steps 376–380 test for the presence of Bovie interference in two different ways by determining two bovie-to-noise (B/N) ratios and then determining whether either of the B/N ratios surpasses a respective threshold. If either surpasses its threshold, Bovie interference is considered to be present.

At step 376, a first B/N ratio is determined in the same way that the S/N ratio was determined at step 346 of the flow routine 304, i.e., based on the difference in power between the two sides of the frequency spectrum. That method of determining the B/N ratio is effective where there is Bovie interference on only one side of the frequency spectrum, as illustrated by FIG. 5c.

However, there may be cases in which the above method of determining the B/N ratio will not be effective. For example, where there are two Bovie interference signals, with one on each side of the frequency spectrum as shown in FIG. 5b, the above method of determining the B/N ratio will not be effective since it is based on the power difference between the two sides of the frequency spectrum and since the two Bovie signals 250, 252 would increase the power on each side of the spectrum by about the same amount, thus effectively canceling each other out.

To account for the case where there is Bovie interference on both sides of the frequency spectrum, an alternative method of determining the B/N ratio is used. In this method, the B/N ratio is based on the average magnitude of the frequency domain samples representing the Bovie interference divided by the average magnitude of all the frequency domain samples in the entire frequency range. More specifically, the B/N ratio is determined as follows:

$$\text{B/N Ratio} = 10 \log [\text{Power}_{Bovie}/\text{Power}_{All}],$$

where $\text{Power}_{Bovie}$ is the average power of the frequency domain samples within a given range of the peak of the Bovie signal and where $\text{Power}_{All}$ is the average power of all the frequency samples in the entire frequency spectrum.

The B/N ratio as determined immediately above for the case of FIG. 5b would be relatively large, signalling the presence of Bovie interference, because the average magnitude of the frequency samples within a given range of the Bovie peak (either peak 250 or peak 252) will be larger than the average of the rest of the frequency samples. The presence of the other Bovie signal (other than the peak) will not significantly raise the average of all the signals due to the relatively small number of such Bovie signals and the relatively large number of all other signals.

Referring back to FIG. 9, the two different B/N ratios are determined at steps 376, 378, and then at step 380 each is compared with a respective threshold, which may be in decibels. If either B/N ratio surpasses its respective threshold, Bovie interference is considered to be present.

Since only Bovie interference that might generate false backflow alarms is of concern, if Bovie interference is detected at step 380, then the routine branches to step 382 where the Bovie frequency determined at step 374 is tested to determine whether it is negative, meaning that it corresponds to negative flow and could therefore produce a false backflow alarm. If it is negative, the routine branches to step 384 where a Bovie detect flag is set to one.

If there was no Bovie interference detected as determined a step 380, or if the Bovie interference that was detected did not correspond to negative flow, then the routine branches to step 386 where the Bovie detect flag is set to zero, or reset.

The status of the Bovie detect flag as determined in steps 384, 386, which is indicative of whether or not Bovie interference was detected during the Bovie routine 306, is used to generate the Bovie flag referred to in step 312 of main routine 300 of FIG. 6, which determines whether or not a backflow alarm will be disabled. The precise relationship between the Bovie and Bovie detect flags is described below in connection with FIG. 10.

Bovie State Diagram

Figure 10:
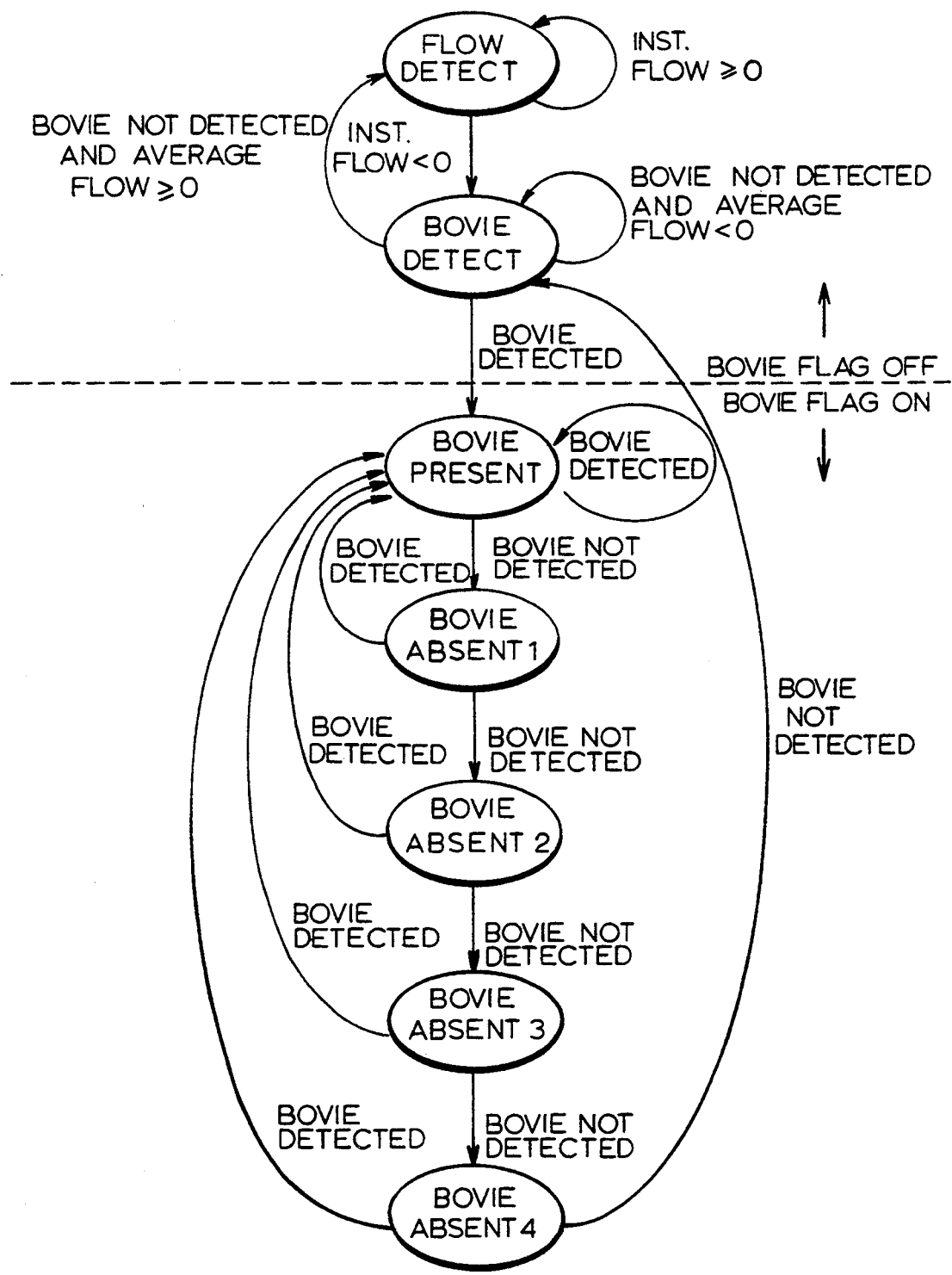
FIG. 10 is a state diagram illustrating a number of states through which the flowmeter may transition when in operation.

Now referring to FIG. 10, the relationship between the Bovie and Bovie detect flags is illustrated with a state diagram, which is typically used to represent the operation of a computer program in which transitions among various states occur based on the present state and certain inputs. In the state diagram of FIG. 10, there are seven possible flowmeter states: a flow detect state, a Bovie detect state, a Bovie present state, and four Bovie absent states.

The current state of the flowmeter determines: 1) when the Bovie routine 306 is executed (when a flexible schedule for the performance of the Bovie routine is used), and 2) when the Bovie flag (which determines when backflow alarms are disabled) is set.

When the flowmeter is in the flow detect state, the Bovie routine 306 is not periodically performed; in all other states, the Bovie routine is periodically performed. When the flowmeter is in either the flow detect or Bovie detect states, the Bovie flag is off; in all other states the Bovie flag is on.

The transition between the flowmeter states is as follows. The flowmeter begins operation in the flow detect state and remains in that state until a negative instantaneous flow is detected (as detected at step 350 of the flow routine 304). As summarized above, when the flowmeter is in the flow detect state, only the flow routine 304, and not the Bovie routine 306, is performed (step 302 of FIG. 6 checks FIG. 10 to determine the current state). Upon the detection of a negative instantaneous flow, the status changes from the flow detect state to the Bovie detect state.

When the flowmeter is in the Bovie detect state, the Bovie routine 306 is periodically performed along with the flow routine 304. If Bovie interference is not detected (as determined by step 386 of the Bovie routine 306) and the average flow (as determined at step 352 of the flow routine 304) is positive, the flowmeter changes back to the flow detect state. If Bovie interference is not detected and the average flow is negative, the flowmeter remains in the Bovie detect state.

If Bovie interference is detected, the flowmeter transitions to the Bovie present state and remains in that state until a subsequent execution of the Bovie routine indicates that Bovie is no longer present (i.e. when the Bovie detect flag is reset at step 386). If Bovie is no longer present, the flowmeter transitions to the first Bovie absent state. From that state, the flowmeter can transition either back to the Bovie present state (if the Bovie detect flag is set at step 384) or to the next Bovie absent state (if the next execution of the Bovie routine 306 again resets the Bovie detect flag at step 386).

If during each subsequent execution of the Bovie routine 306 the Bovie detect flag is reset, the flowmeter proceeds through the Bovie absent states and back to the Bovie detect state. If at any time the flowmeter is in a Bovie absent state and the Bovie routine 306 sets the Bovie detect flag, the flowmeter transitions back to the Bovie present state.

When the flowmeter is in the Bovie present state or any of the Bovie absent states, which are shown below the dotted line shown in FIG. 10, the Bovie flag is turned on. In the two states above the dotted line, the Bovie flag is turned off. Thus, the backflow alarm is disabled (see step 312 of FIG. 6) when the flowmeter is in any of the states below the dotted line. As can be appreciated from FIG. 10, once a Bovie is detected, hysteresis is used to maintain the Bovie flag on for a given time period.

As an alternative, the flowmeter may be utilized without the Bovie hysteresis described in connection with FIG. 10. In that case, during step 312 of FIG. 6, the flowmeter would check the status of the Bovie detect flag of the Bovie routine of FIG. 6 instead of the Bovie flag of FIG. 10.

Additional Embodiment

As described above, Bovie interference is detected by periodically reading the receiver 130 without sending an excitation signal via the transmitter 120. In cases where a transmitter is not used, such as in the case of a flowmeter using an electromagnetic probe, a test channel could be utilized to check for electrical interference in addition to the normal flow channel. A probe not requiring an active signal for operation is referred to herein as a passive probe.

Figure 11:
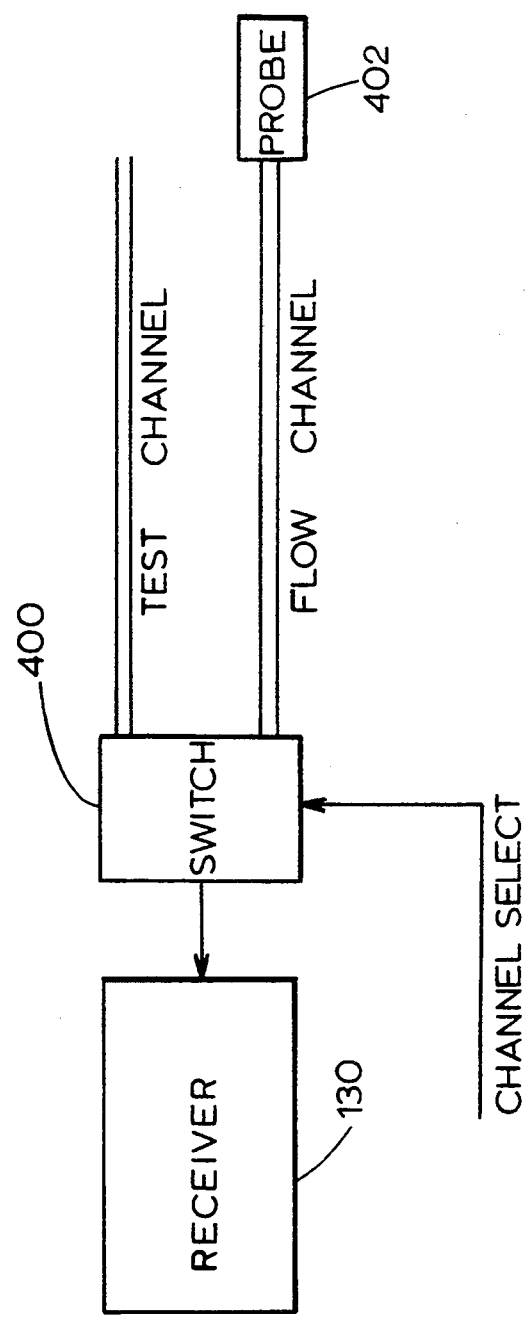
FIG. 11 illustrates a portion of an alternative embodiment of the invention.

Referring to FIG. 11, an alternative embodiment includes the receiver 130 connected to a multiplexer or switch 400 connected to a flow channel utilizing a passive probe and to a test channel not having any type of probe. The characteristics of the test channel, e.g. length location, material, etc., should approximate the flow channel as closely as possible.

During operation of the flowmeter with a passive probe and no transmitter, the receiver 130 would read the flow channel during the flow routine 304 and would read the test channel during the Bovie routine 306.

Numerous other modifications and alternative embodiments will be apparent to those skilled in the art in view of the foregoing description. This description is to be construed as illustrative only, and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A blood pumping system having a backflow warning system that selectively generates a warning of blood backflow through a non-occlusive blood pump, said blood pumping system comprising:
   a non-occlusive blood pump;
   a conduit connected to said non-occlusive blood pump, said conduit being connectable to a patient so as to enable venous blood flow from the patient to said blood pump and to enable arterial blood flow from said blood pump back to the patient;
   an electrical interference detector that determines the presence of electrical interference that could cause a false backflow warning; and
   a backflow warning generator coupled to said electrical interference detector that selectively generates a backflow warning, said backflow warning generator generating a backflow warning upon the detection of a backflow condition in the absence of said electrical interference as determined by said electrical interference detector.

2. A system as defined in claim 1 wherein said backflow warning comprises a backflow alarm and wherein said backflow condition comprises negative blood flow through said conduit.

3. A system as defined in claim 1 wherein said electrical interference comprises Bovie interference generated by an electrocauterizer unit.

4. A system as defined in claim 1 wherein said backflow warning generator generates a backflow warning upon the detection of a backflow condition only in the absence of electrical interference of a frequency that would otherwise cause a false backflow warning.

5. A system as defined in claim 1 wherein said interference detector comprises:
   a receiver that periodically generates a signal relating to electrical interference; and
   a threshold detector coupled to said receiver that determines when said electrical interference surpasses a threshold.

6. A system as defined in claim 5 wherein said threshold comprises a constant.

7. A system as defined in claim 1 additionally comprising a transmitter that generates a periodic electrical excitation signal and a transmitter probe coupled to said transmitter that converts said electrical excitation signal into ultrasonic energy and radiates said ultrasonic energy into said conduit, and wherein said interference detector comprises:
   a receiver probe that receives reflections of said ultrasonic energy radiated by said transmitter probe and converts said ultrasonic energy reflections into an electrical receive signal;
   a receiver coupled to said receiver probe that generates a first signal from said electrical receive signal when said transmitter is activated and a second signal from electrical interference when said transmitter is not activated; and
   a threshold detector coupled to said receiver that determines when said electrical interference surpasses a given threshold.

8. A system as defined in claim 7 wherein said threshold is a predetermined number of decibels.

9. A system as defined in claim 7 wherein said electrical interference comprises Bovie interference generated by an electrocauterizer unit.

10. A medical apparatus having a warning system that selectively generates a warning only in the absence of electrical interference, said medical apparatus comprising:
    an electrical interference detector that determines the presence of electrical interference that could cause a false warning by (step d of claim 12);
    a medical condition detector for detecting the presence of an adverse medical condition; and
    a medical warning generator coupled to said electrical interference detector and said medical condition detector, said medical warning generator selectively generating a medical warning upon the detection of an adverse medical condition only in the absence of said electrical interference as determined by said electrical interference detector.

11. A medical apparatus as defined in claim 10 wherein said interference detector comprises:
    a receiver that periodically generates a signal relating to electrical interference; and
    a threshold detector coupled to said receiver that determines when said electrical interference surpasses a threshold.

12. A medical apparatus as defined in claim 11 wherein said threshold comprises a constant.

13. A medical apparatus as defined in claim 10 additionally comprising a transmitter that generates a periodic electrical excitation signal and a transmitter probe coupled to said transmitter that converts said electrical excitation signal into ultrasonic energy and radiates said ultrasonic energy into said conduit, and wherein said interference detector comprises:
    a receiver probe that receives reflections of said ultrasonic energy radiated by said transmitter probe and converts said ultrasonic energy reflections into an electrical receive signal;
    a receiver coupled to said receiver probe that generates a first signal from said electrical receive signal when said transmitter is activated and a second signal from electrical interference when said transmitter is not activated; and
    a threshold detector coupled to said receiver that determines when said electrical interference surpasses a given threshold.

14. A medical apparatus as defined in claim 13 wherein said threshold is a predetermined number of decibels.

15. A medical apparatus as defined in claim 13 wherein said electrical interference comprises Bovie interference generated by an electrocauterizer unit.

16. A medical apparatus as defined in claim 10 wherein said interference detector comprises a test channel, said medical apparatus additionally comprising a sensing channel and a probe attached to said sensing channel.

17. A blood pumping system having a backflow warning system that selectively generates a warning of blood backflow through a non-occlusive blood pump, said blood pumping system comprising:
    a non-occlusive blood pump;
    a conduit connected to said non-occlusive blood pump, said conduit being connectable to a patient so as to enable venous blood flow from the patient to said blood pump and to enable arterial blood flow from said blood pump back to the patient;
    a transmitter that generates a periodic electrical excitation signal;
    a transmitter probe coupled to said transmitter that converts said electrical excitation signal into ultrasonic energy and radiates said ultrasonic energy into said conduit;

a receiver probe that receives reflections of said ultrasonic energy radiated by said transmitter probe and converts said ultrasonic energy reflections into an electrical receive signal;

a receiver coupled to said receiver probe that generates a first signal from said electrical receive signal when said transmitter is activated and a second signal from electrical interference when said transmitter is not activated;

a threshold detector coupled to said receiver that determines when said second signal surpasses a threshold; and a backflow warning generator coupled to said receiver that selectively generates a backflow warning, said backflow warning generator not generating a backflow warning when said second signal surpasses a threshold as determined by said threshold detector.

18. A method of selectively generating a backflow warning in a blood pumping system in response to the detection of a blood backflow condition, said method comprising the steps of:
(a) connecting the arterial and venous systems of a patient to a conduit through which blood is pumped via a blood pump;
(b) activating a transmitter which transmits an electrical excitation signal to a transmit probe to generate ultrasonic energy in the conduit;
(c) while said transmitter is activated during said step (b), receiving electrical signals via a receiver which are indicative of blood flow through the conduit;
(d) periodically searching for the presence of electrical interference that could cause a false warning by receiving electrical signals via the receiver while the transmitter is not activated;
(e) detecting the presence of a backflow condition relating to blood backflow through the conduit; and
(f) generating a backflow warning when the presence of the backflow condition is detected in said step (e) in the absence of electrical interference searched for in said step (d).

19. A method as defined in claim 18 wherein said electrical interference comprises Bovie interference.

20. A method as defined in claim 18 additionally comprising the step of (g) determining the frequency of said electrical interference and wherein a backflow warning is generated during said step (f) only when the frequency of said electrical interference corresponds to blood backflow.

21. A method as defined in claim 18 wherein said step (d) searches for said electrical interference by the steps of (d1) generating an interference-to-noise ratio and (d2) comparing said interference-to-noise ratio with a threshold.

22. A method of selectively generating a backflow warning in a blood pumping system in response to the detection of a blood backflow condition, said method comprising the steps of:
(a) connecting the arterial and venous systems of a patient to a conduit through which blood is pumped via a blood pump;
(b) activating a transmitter which transmits an electrical excitation signal to a transmit probe to generate ultrasonic energy in the conduit;
(c) while said transmitter is activated during said step (b), receiving electrical signals via a receiver which are indicative of blood flow through the conduit;
(d) periodically searching for the presence of electrical interference that could cause a false backflow warning by receiving electrical signals via the receiver while the transmitter is not activated, said step (d) comprising the steps of:
(d1) generating a first interference-to-noise ratio;
(d2) comparing said first interference-to-noise ratio with a first threshold;
(d3) generating a second interference-to-noise ratio; and
(d4) comparing said second interference-to-noise ratio with a second threshold;
(e) detecting the presence a backflow condition relating to blood backflow through the conduit; and
(f) generating a backflow warning when the presence of the backflow condition is detected in said step (e) in the absence of electrical interference searched for in said step (d).

* * * * *